United States Patent
Reitzel et al.

(10) Patent No.: US 9,068,156 B2
(45) Date of Patent: Jun. 30, 2015

(54) HORIZONTAL PLATE MICROBIAL SUPPORT MEDIA

(75) Inventors: John S. Reitzel, Brookfield, VT (US); Gail Leslie Reitzel, legal representative, Brookfield, VT (US); William C. Stewart, Caldwell, ID (US)

(73) Assignee: Advanced Bio Energy Development LLC, Caldwell, ID (US)

( * ) Notice: Subject to any disclaimer, the term of this patent is extended or adjusted under 35 U.S.C. 154(b) by 763 days.

(21) Appl. No.: 13/056,869

(22) PCT Filed: Jul. 31, 2009

(86) PCT No.: PCT/US2009/052407
§ 371 (c)(1),
(2), (4) Date: Jan. 31, 2011

(87) PCT Pub. No.: WO2010/014902
PCT Pub. Date: Feb. 4, 2010

(65) Prior Publication Data
US 2011/0259804 A1    Oct. 27, 2011

Related U.S. Application Data

(60) Provisional application No. 61/085,244, filed on Jul. 31, 2008.

(51) Int. Cl.
*C12M 1/00* (2006.01)
*C02F 3/28* (2006.01)

(52) U.S. Cl.
CPC .............. *C12M 23/34* (2013.01); *C12M 27/22* (2013.01)

(58) Field of Classification Search
CPC . C02F 2003/008; C12M 21/00; C12M 21/04; C12M 25/02; C12M 25/04; C12M 25/06; C12M 25/14; B09C 1/10; C12P 1/00; C12N 1/12; C12N 1/10; C12N 1/20; C05F 17/0027; C05F 17/0247; C05F 17/0252; C05F 17/0288; C05F 17/0294
USPC ......... 210/150, 252, 255, 256, 615, 616, 617, 210/630; 261/101–13, 112.1, 112.2, 110, 261/113; 435/287.8, 287.9, 288.2, 289.1, 435/291.3, 303.2, 304.2, 305.2
See application file for complete search history.

(56) References Cited

U.S. PATENT DOCUMENTS 1,749,266 A * 3/1930 Sontag ........................... 261/113
2,639,035 A * 5/1953 Pearlstein ..................... 210/489

(Continued)

FOREIGN PATENT DOCUMENTS

WO        2006/122088 A1    11/2006

OTHER PUBLICATIONS

Cheng, K.-C. and et al., Advances in biofilm reactors for production of value-added products. Appl. Microbiol. Biotech., 2010. 87: p. 445-456.

(Continued)

*Primary Examiner* — Allison Fitzsimmons
(74) *Attorney, Agent, or Firm* — Buchanan Nipper

(57) ABSTRACT

A horizontal plate microbial support media. The horizontal plate microbial support media having a plurality of frustum shaped protuberances extending there-from, the frustum shapes having a hole in their upper base for allowing fluid to flow there-through. These media plates able to be stacked for use in a bioreactor.

19 Claims, 5 Drawing Sheets

(56) References Cited

U.S. PATENT DOCUMENTS

| | | | | |
|---|---|---|---|---|
| 2,853,195 | A | * | 9/1958 | Malcolm .................. 210/471 |
| 2,910,183 | A | * | 10/1959 | Hayes ...................... 210/315 |
| 4,137,172 | A | * | 1/1979 | Sako et al. ................ 210/150 |
| 4,321,064 | A | * | 3/1982 | Vargo ......................... 95/272 |
| 4,345,997 | A | * | 8/1982 | McConnell et al. ...... 210/150 |
| 4,956,085 | A | | 9/1990 | Kopf |
| 5,049,268 | A | | 9/1991 | Kopf |
| 5,232,589 | A | | 8/1993 | Kopf |
| 5,388,316 | A | | 2/1995 | MacLaren |
| 5,389,248 | A | | 2/1995 | Pare et al. |
| 5,545,327 | A | | 8/1996 | Volland |
| 6,036,863 | A | | 3/2000 | Brockdorff |
| 6,241,222 | B1 | | 6/2001 | Lang |
| 6,274,035 | B1 | | 8/2001 | Yuan et al. |
| 2009/0152195 | A1 | * | 6/2009 | Rodgers et al. ........... 210/615 |

OTHER PUBLICATIONS

Wang, Z-W. and S. Chen, Potential of Biofilm-Based Biofuel Production. Appl. Microbiol. Biotechnol., 2009. 83: p. 1-18.

Wuertz, S. and et al., Microbial Communities and Their Interactions in Biofilm Systems: an Overview. Wat. Sci. & Tech., 2004. 49(11-12): p. 327-336.

Rosche, B. and et al., Microbial Biofilms: A Concept For Industrial Catalysis. Trends in Biotech., 2009. 27(11): p. 636-643.

Young, J. and M. Dahab, Effect of Media Design on the Performance of Fixed-Bed Anaerobic Reactors. Wat. Sci. Tech., 1983. 15(8-9): p. 369-383.

Pangarkar, K. and et al., Structured Packings for Multiphase Catalytic Reactors. Ind. Eng. Chem., 2008. 47: p. 3720-3751.

Escudie, R. and et al., Review—Control of start-up and operation of anaerobic biofilm reactors: An overview of 15 years of research. Wat. Res., 2011. 45: p. 1-10.

Boltz, J. and et. al., Mathematical modelling of biofilms and biofilm reactors for engineering design. Wat. Sci. Tech., 2010. 62(8): p. 1821-1836.

Monds, R.D. and G.A. O'Toole, The Developmental Model of Microbial Biofilms: Ten Years of a Paradigm Up For Review. Trends in Microbiology, 2009. 17(2): p. 73-87.

Written Opinion, PCT/US2009/052407, dated Oct. 7, 2009.

International Search Report, PCT/US2009/052407, dated Oct. 7, 2009.

* cited by examiner

HORIZONTAL PLATE MICROBIAL SUPPORT MEDIA

BACKGROUND

In nature, microbial communities in fluid environments attach to solid substrates (e.g., rocks, sand granules) to form biofilms. Biofilms are aggregations of microorganisms attached to a submerged surface, affording a protective matrix for complex community interactions. These biofilms also increase the resistance of microbes to environmental perturbations (e.g., temperature changes, toxins).

In engineered bioreactors, permanent fixed surfaces (aka "biological attachment surfaces" and "microbial support media") are commonly provided as attachment sites for development of biofilms. Such engineered bioreactors include those used in water and wastewater treatment facilities, toxic waste remediation processes, pharmaceutical and chemical manufacturing processes, and renewable fuel production.

Operational advantages to the use of such microbial support media include: (1) increased system stability and reliability; (2) increased microbial productivity; (3) decreased reactor size requirements; (4) minimization of microbial loss when product is removed from the reactor; and (5) significantly greater resistance to environmental stresses such as temperature or pH fluctuations and exposure to toxins.

Types of Microbial Support Media. There are two broad classifications of microbial support media commonly used in industry, namely (1) "Random Media" and (2) "Modular Media."

Random Media (also known as "Dumped Media") comprises individual pieces of media which are randomly placed into a bioreactor. Random Media can comprise a wide variety of material including, but not limited to, lava rock chunks and various shapes of synthetic media (e.g., perforated balls, saddles, pall rings).

There are a number of problems inherent in the use of Random Media as a microbial support media, including: (1) Random Media can have an inconsistent pore space between individual microbial support media pieces, thereby resulting in uneven hydraulic flow through the microbial support media, increased backpressure and reduced substrate contact with the attached biofilm; (2) Random Media typically has relatively low specific surface area for microbial attachment; and (3) due to its configuration, uneven biomass buildup can occur in Random Media, this buildup resulting in a long-term increase in pore blockage and hydraulic short circuiting.

Modular Media (also knows as "Sheet Media") typically comprises formed sheets, usually made of PVC plastic, which are joined together. There are two main types of modular media, namely, simple vertical tubes and vertical cross-flow tubes. In vertical cross-flow tubes, the tubes intersect at opposite angles (e.g., sixty degrees), thereby increasing mixing. Both types of modular media were developed originally for air systems. In biological applications, they are currently used primarily in down-flow aerobic trickling filter systems for wastewater treatment.

Modular media poses a number of problems, particularly when applied to upflow anaerobic reactors, namely that (1) the tubular media has poor mixing characteristics and tends to be susceptible to aperture blockage due to biomass buildup, particularly at the interface where modules are stacked, and (2) the cross flow media has good mixing characteristics in high fluid velocity situations such as down-flow trickling filters, however, in the low upward fluid velocities characteristic of anaerobic reactors, laminar flow occurs, reduced mixing characteristics occurs, and reduced contact of substrate with the attached biofilm occurs.

DESCRIPTION OF THE PREFERRED EMBODIMENTS

Figure 1:
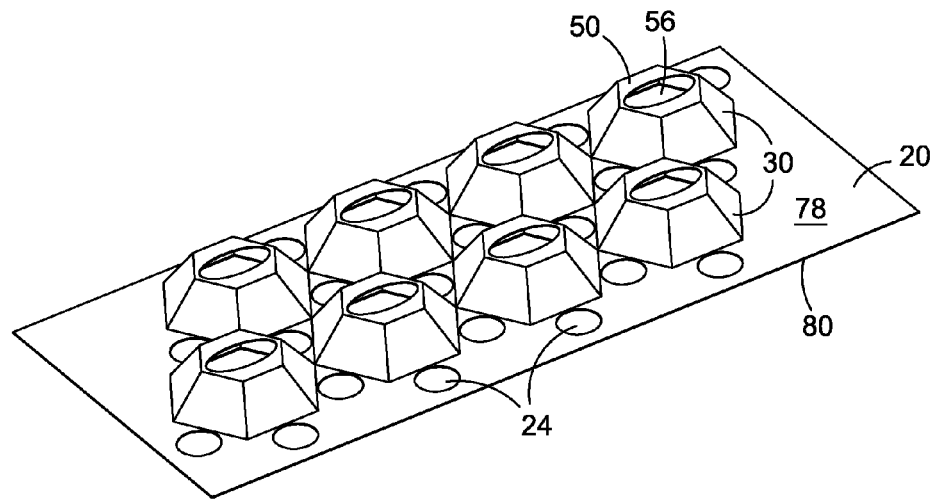
FIG. 1 is a perspective view of a first embodiment of the present invention.

While the invention is susceptible of various modifications and alternative constructions, certain illustrated embodiments thereof have been shown in the drawings and will be described below in detail. It should be understood, however, that there is no intention to limit the invention to the specific form disclosed, but, on the contrary, the invention is to cover all modifications, alternative constructions, and equivalents falling within the spirit and scope of the invention as defined in the claims.

In the following description and in the figures, like elements are identified with like reference numerals. The use of "e.g.," "etc," and "or" indicates non-exclusive alternatives without limitation unless otherwise noted. The use of "including" means "including, but not limited to," unless otherwise noted.

The present invention is a horizontal plate microbial support media (also referred to herein as the "support media" and as a "filter plate"). The support media was specifically designed to optimize both the hydraulic and biological functionality of upflow anaerobic processes.

Figure 2:
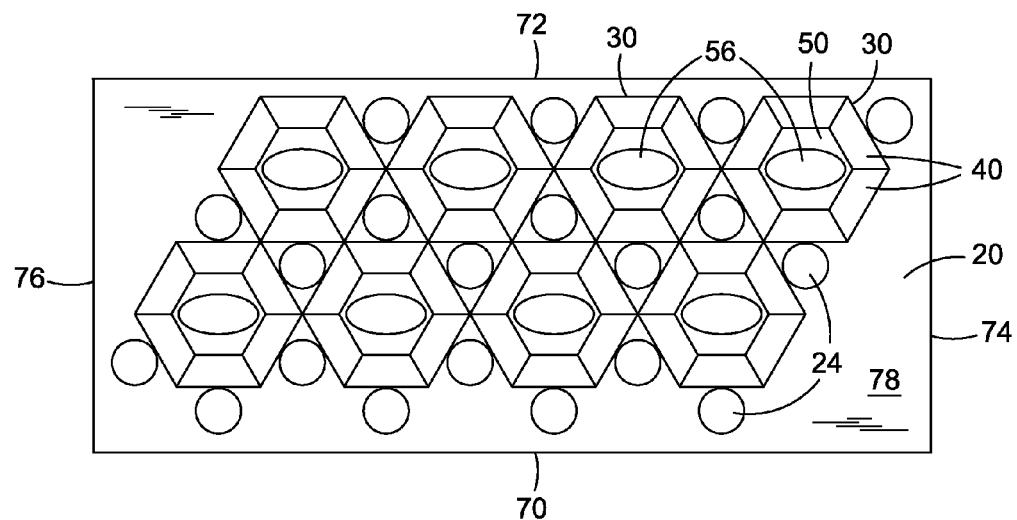
FIG. 2 is a plan view of the embodiment of FIG. 1.

The support media is preferably thermoformed or stamped from suitable material (e.g., a polyvinyl chloride (PVC) sheet, a polypropylene (PP) sheet, a metal sheet) such as the sheet 20 shown in FIGS. 1 and 2. The thickness used can be varied based upon the application.

The support media 20 preferably provided on a generally rectangular, generally planar sheet having a first end edge 70 and a second end edge 72 at respective opposing longitudinal ends thereof defining a width of the support media 20 there-between, a first side edge 74 and a second side edge 76 at respective opposing lateral ends thereof defining a length of the support media 20 there-between, where the sides and ends defining a top surface 78 and a bottom surface 80.

It is preferred that a plurality of protuberances 30 be formed extending from one or more of the top or bottom surfaces, preferably from the top surface 78. It is preferred that protuberances be generally equidistantly spaced apart.

The protuberances 30 can be any number of shapes, but are preferably shaped like a frustum, having a bottom plane (bottom base) defined by the top surface 78 (or the bottom surface 80) of the support media 20 and a top plane 50 (top base)

spaced there-from. The frustum having at least one face 40 extending between the top base and bottom base. Preferred frustum shapes include oval frustums and frustums having three or more sides (e.g., hexagonal frustums, heptagonal frustums, octagonal frustums). A right, hexagonal frustum (as shown in the Figures) being the most preferred. Other frustum shapes are also possible.

Figure 3A:
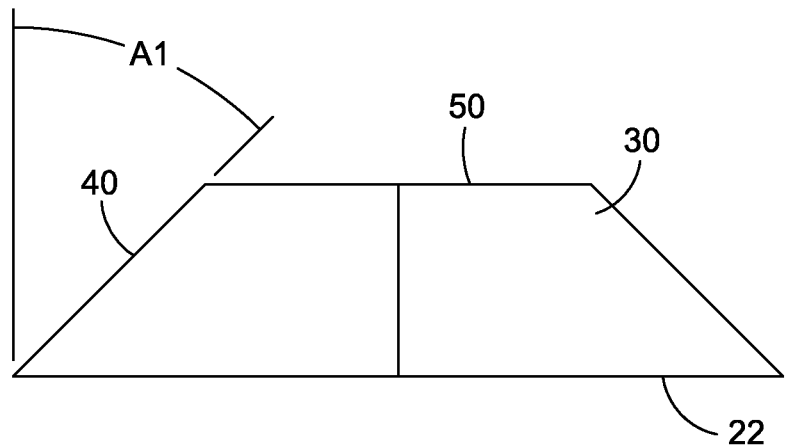
FIG. 3A is a partial, side view of a forty-five degree angled protrusion.
Figure 3B:
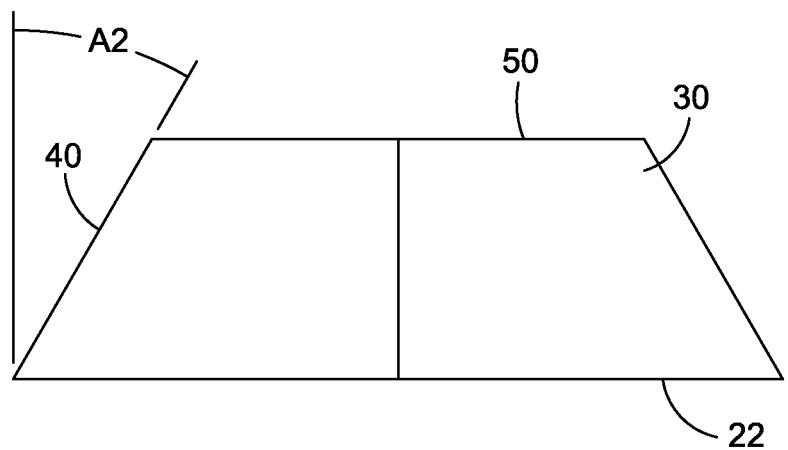
FIG. 3B is a partial, side view of a sixty degree angled protrusion.

In the preferred embodiment, the faces 40 intersect the bottom base 22 at a 20° to 80° angle, with 45° to 60° being more preferred. A face angle (A1) of 45°, as shown in FIG. 3A, is preferred where solids loading is low for final effluent polishing to increase surface area per unit volume. FIG. 3B showing a 60° face angle (A2).

The height of the protuberances 30 (distance between the two frustum bases) can be varied based upon the application. Preferred heights include from 1.00 inch (2.54 cm) to 12.00 inches (30.48 cm) or more.

It is preferred that an elongate or oval hole (passageway) 56 be defined in the top base 50 for allowing fluid communication with overlaying horizontal sheets.

Preferably, at least one sheet hole 24 be defined through the sheet 20 adjacent and/or in between the protuberances 30. The sheet holes allow any solids or sludge which may build up at the base of the protuberances to be removed by reversing the flow in the reactor (from upward flow to downward flow) for a period of time. This step may need to be done occasionally to prevention of any blockage due to excessive buildup of solids on the horizontal flat sheet portion between the protuberances.

A staggered layout is preferred, this staggered layout allowing individual sheets 20 of the present invention to be stacked into modules (for use in a reactor vessel) by rotating certain of the sheets (for instance, every other sheet) in the stack. For instance, in one configuration, every other sheet could be rotated 180 degrees. Having a staggered layout, the sheets would not nest when so rotated and would form a vertical structure (as shown in FIG. 4), the "stacked formation." However, when manufactured, shipped and stored, the sheets can be stacked in a nested fashion, saving space (the "nested formation").

Figure 4:
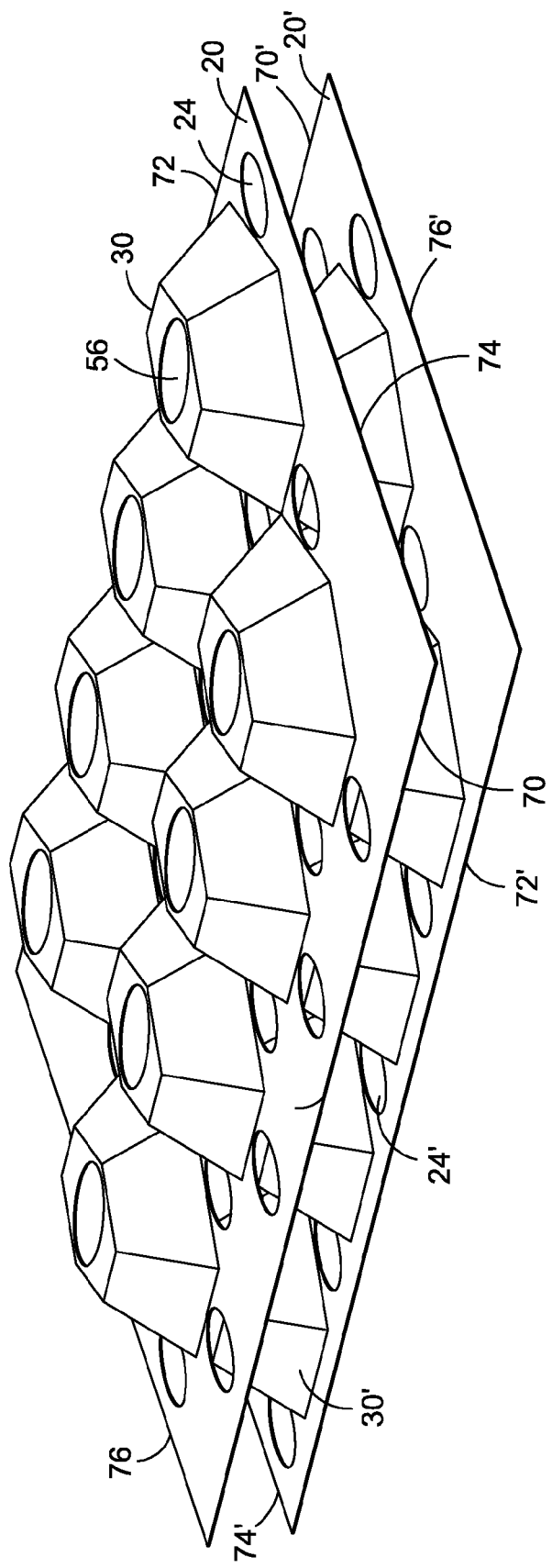
FIG. 4 is a perspective view of two of the sheets of FIG. 1 shown in a stacked, spaced configuration.

FIG. 4 showing a first sheet 20 stacked upon a second sheet 20'. In this configuration, the first sheet 20 is identical to the second sheet 20', however the first sheet 20 has been rotated in the plane of the bottom base 180 degrees. The second sheet (support media) 20' preferably provided on a generally rectangular, generally planar sheet having a first end edge 70' and a second end edge 72' at respective opposing longitudinal ends thereof defining a width of the support media 20' therebetween, a first side edge 74' and a second side edge 76' at respective opposing lateral ends thereof defining a length of the support media 20' there-between, where the sides and ends defining a top surface 78' and a bottom surface 80'. The second sheet 20' having protuberances 30' which support the underside of the first sheet. The figure also showing a plurality of sheet holes 24' in the second sheet.

It is preferred, but not necessary, that when in the stacked formation an adhesive or other means of joining the sheets together (e.g., sonic welding, fasteners, glue) permanently or semi-permanently could be utilized. In such a configuration, the media is self-supporting (it does not rely on reactor vessel walls for support or produce lateral forces against the reactor vessel walls). Again, such a staggered configuration allows the media sheets to be stacked tightly for compact shipping, yet allows them to be easily assembled on the job site without special tools.

Figure 5:
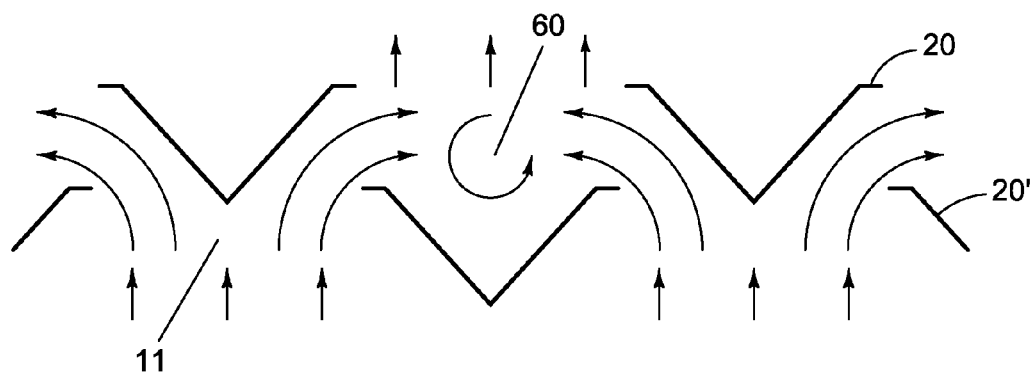
FIG. 5 is a partial, side representation of flow through of a first configuration.
Figure 6:
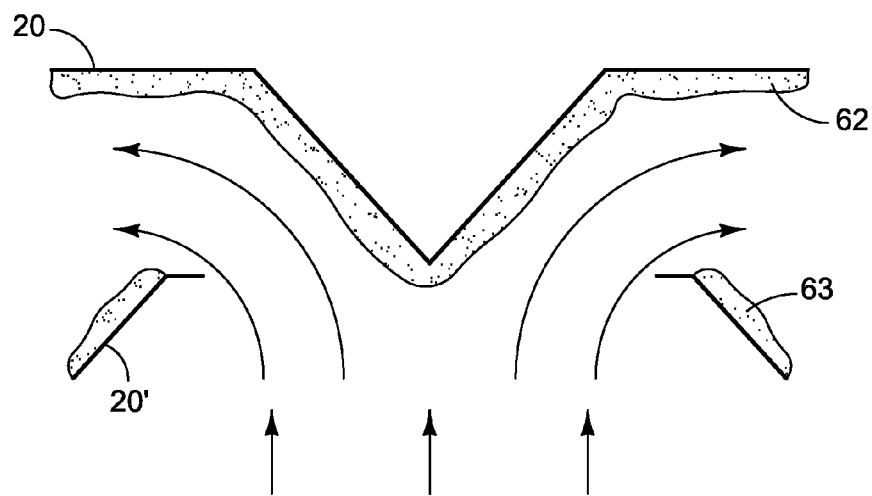
FIG. 6 is a partial, side representation of flow through of a second configuration.

FIGS. 5-8 show various partial cross-sectional views representing what the hydraulic flows in stacked configurations could look like. FIG. 5, shows potential hydraulic attributes present. In that figure, an upper sheet is stacked upon a lower sheet, these stacked sheets forming individual cells which impose flow splitting 11 and remixing 60 at low upflow velocities found in anaerobic reactors. This significantly reduces and/or eliminates potential channeling effects. As can be seen in FIG. 6, such a design also imposes impingement against upper surface of media sheets prior to flow splitting and remixing.

Biologically, the support media 20 provides a stable attachment site for biofilm development, minimizing washout (loss of microorganisms) and maximizing process stability. The flow splitting, mixing, remixing, and flow impingement at the upper media surface, characteristic of the design, ensures even distribution of substrate throughout the reactor volume and maximizes contact with the biologically active media surfaces (as is illustrated in FIGS. 5 and 6).

The enforced impingement of liquid at the upper media surface, which insures contact with the microbial biofilm attached to this surface (FIG. 6), accelerates capture, agglomeration, and removal of suspended and colloidal solids from the upflowing carrier fluid. As these agglomerated solids build up, they drop off the upper surface 62 to the lower surface 63 (shown in FIG. 6) where further digestion takes place.

The enforced impingement of product against the upper media surface also increases contact and entrapment with rising gases such as carbon dioxide ($CO_2$) and hydrogen ($H_2$) released in the hydrolysis and acidogenesis reactions of anaerobic digestion. Conversion of these gases by the methane ($CH_4$) producing microorganisms attached to the upper surface of a media cell is enhanced producing a higher BTU biogas in that it contains more methane ($CH_4$) and less carbon dioxide ($CO_2$).

The enforced impingement of product against the upper media surface also increases contact of soluble low-molecular weight organics (e.g., acetate) released in the acidogenesis phase reactions of methane production. Conversion of these organics by the methane producing microorganisms attached to the upper surface of a media cell is enhanced, producing larger quantities of methane ($CH_4$) gas.

The provision of an upper and lower attachment surface permits the establishment of a multi-phased biological system within the media. For example, solids digestion takes place on the lower surface of a cell, while the capture and digestion of the soluble end products of the solids digestion takes place by the biofilm attached to the upper layer of the media. This reduces potential competitive interactions between the two communities. This multi-phased mechanism is particularly important in protecting methane ($CH_4$) producing microorganisms (attached to the upper surface) from competition with the more robust hydrolysis and acidogenesis bacteria on the lower digestive surface.

Figure 7:
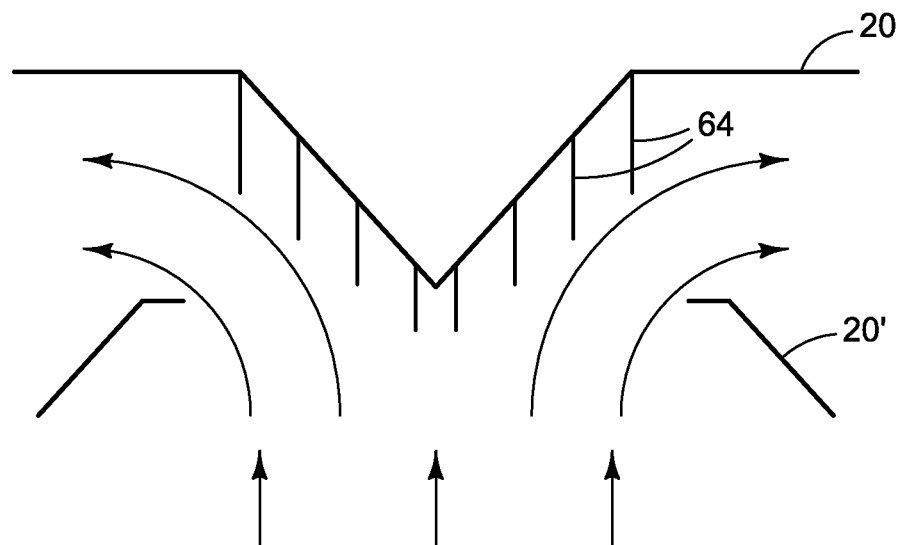
FIG. 7 is a partial, side representation of flow through of a third configuration.

The horizontal plate design also permits roughing (e.g., sandblasting, spraying on a coating) of upper surface to improve adhesion of biofilm and/or addition of elongate stalactite-like biofilm attachment projections 64 on upper surface of media to increase surface area for biofilm attachment, as is illustrated in FIG. 7.

Figure 8:
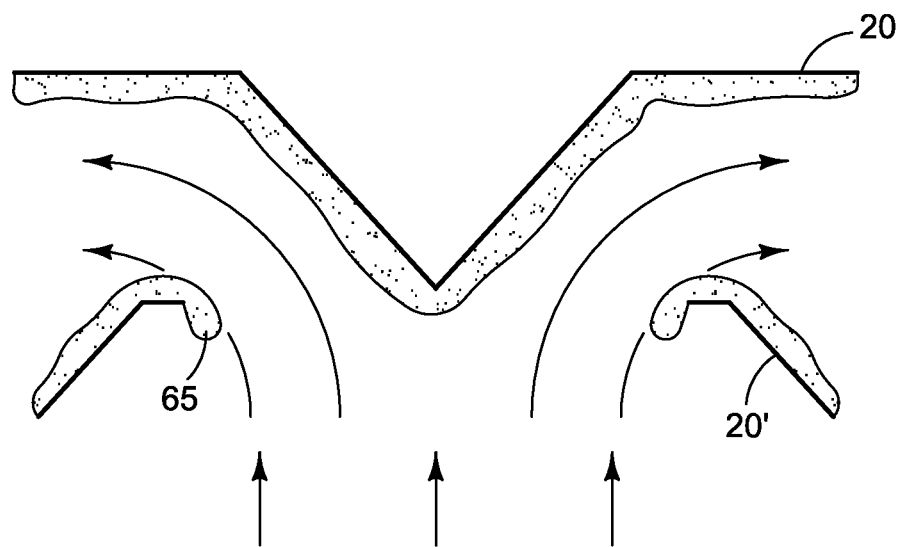
FIG. 8 is a partial, side representation of flow through of a fourth configuration.

The provision of edges 65 at the openings of the media induces accelerated and heavy growth of biofilm at these edges in response to food availability thus increasing specific biological activity, as is illustrated in FIG. 8.

Media Countercurrent Flow Application for Ethanol, Pharmaceuticals and Other Applications. In many biotechnology manufacturing operations, gases (e.g., carbon dioxide ($CO_2$), hydrogen ($H_2$)) are formed as waste products or metabolic by-products. These gases, as their concentration increases, can impede biological production of the desired product due to inhibitory effects. To alleviate this effect, the Horizontal Plate Microbial Support Media can be used in a countercurrent flow application in which the liquid stream carrying the food material and resultant product flows in a downward direction in a reactor packed with the media. The microorganisms performing the transformation will then be found at highest concentrations on the lower surface of the media. Inhibitory gases, such as carbon dioxide ($CO_2$), will rise upward against this liquid flow. These gases will primarily contact the upper surface of the media sheets, protecting the active biofilm on the lower surface from full contact with these inhibitory gases.

In cases where such countercurrent flow is desirable, the media can be modified to increase biofilm formation and surface area by roughing the lower surface (e.g. sandblasting, spraying on a coating) and/or addition of elongate stalagmite-like biofilm attachment projections (as opposed to the stalactite like biofilm attachment projections 64 shown on the upper surface of a cell in FIG. 7) on the lower surface of the media to increase surface area for biofilm attachment. Other liquid downward flow applications in which countercurrent flow of a liquid and a gas can be applied include aerobic and anaerobic reactors such as wastewater trickling filters, air pollution trickling filters and various pharmaceutical and other biotechnology manufacturing reactors.

The basic media design approach can also be applied as media in cooling towers, mist eliminators, tube or plate settlers, biofilter trickling filters, wastewater trickling filters, aerobic submerged media wastewater treatment reactors, ethanol production reactors, and pharmaceutical product reactors, among other applications.

A first example embodiment. A filter medium for allowing a flow of a liquid there-through, said medium comprising: a vertical stack of adjacent generally rectangular sheets having a first end edge and a second end edge at respective opposing lateral ends, a first side edge and a second side edge at respective opposing longitudinal ends, said sides and ends defining a top surface and a bottom surface, said sheets having a plurality of frustum-shaped protuberances extending from said top surface, said frustum-shape having a bottom base defined by the top surface of the sheet and a top base spaced there-from, the frustum having at least one face extending between the top base and bottom base, wherein said at least one face intersects the bottom base at a 45° to 60° angle, said top base further comprising a passageway defined there-through; wherein adjacently stacked sheets are arranged so as to create non-linear flow paths.

A second example embodiment. A generally rectangular, generally planar filter plate, said plate comprising: a sheet having a first end edge and a second end edge at respective opposing longitudinal ends, a first side edge and a second side edge at respective opposing lateral ends, said sides and ends defining a top surface and a bottom surface; and a plurality of frustum-shaped protuberances extending from said top surface, said frustum-shape having a bottom base defined by the top surface of the sheet and a top base spaced there-from, the frustum having at least three faces extending between the top base and bottom base, wherein said faces intersect the bottom base at a 45° to 60° angle, said top base further comprising a passageway defined there-through.

A third example embodiment. First and second generally identical filter plates, said filter plates configured for stacking, each of said filter plates comprising: a generally rectangular, generally planar sheet having a first end edge and a second end edge at respective opposing longitudinal ends, a first side edge and a second side edge at respective opposing lateral ends, said sides and ends defining a top surface and a bottom surface, a plurality of frustum-shaped protuberances extending from said top surface, each of said frustum-shaped protuberances having generally matching frustum-shaped recesses formed in said bottom surface, said frustum-shape protuberance having a bottom base defined by the top surface of the sheet and a top base spaced there-from, the frustum having at least three faces extending between the top base and bottom base, wherein said faces intersect the bottom base at a 45° to 60° angle, said top base further comprising a passageway defined there-through; wherein said first filter plate and said second filter plate are configured to stack together in a nesting configuration with the frustum-shaped protuberances of the first filter plate being received into the frustum-shaped recesses of said second filter plate; wherein said first filter plate can be rotated so that said first filter plate and said second filter plate are configured to stack together in a vertically spaced configuration wherein said first filter plate's top bases contact said second filter plate's bottom surface thereby spacing said first filter plate apart from said second filter plate.

While there is shown and described the present preferred embodiment of the invention, it is to be distinctly understood that this invention is not limited thereto but may be variously embodied to practice within the scope of the following claims. From the foregoing description, it will be apparent that various changes may be made without departing from the spirit and scope of the invention as defined by the following claims.

The purpose of the Abstract is to enable the public, and especially the scientists, engineers, and practitioners in the art who are not familiar with patent or legal terms or phraseology, to determine quickly from a cursory inspection, the nature and essence of the technical disclosure of the application. The Abstract is neither intended to define the invention of the application, which is measured by the claims, nor is it intended to be limiting as to the scope of the invention in any way.

Still other features and advantages of the claimed invention will become readily apparent to those skilled in this art from the following detailed description describing preferred embodiments of the invention, simply by way of illustration of the best mode contemplated by carrying out my invention. As will be realized, the invention is capable of modification in various obvious respects all without departing from the invention. Accordingly, the drawings and description of the preferred embodiments are to be regarded as illustrative in nature, and not as restrictive in nature.

What is claimed is:

1. A microbial support media system for an upward flow microbial digestion system, comprising:
    a first horizontal plate microbial support media having a first upper surface and a first lower surface, the first horizontal plate microbial support media having a plurality of first protuberances, each of the first protuberances having a first base and a first upward end, each of the first protuberances extending upward from the first upper and lower surfaces at the first base to the first upward end in such a way that the first base of each of the first protuberances is wider than the first upward end, each first upward end having a first opening for allowing the upward flow of a liquid to pass through;
    a second horizontal plate microbial support media having a second upper surface and a second lower surface, the second horizontal plate microbial support media having a plurality of second protuberances, each of the second protuberances having a second base and a second upward end, each of the second protuberances extending upward from the second upper and lower surfaces at the second base to the second upward end in such a way that the second base of each of the second protuberances is wider than the second upward end, each second upward end having a second opening for allowing the upward flow of the liquid to pass through, the first horizontal plate microbial support media is disposed above the second horizontal plate microbial support media in such a way that the plurality of first protuberances and the plurality of second protuberances are offset a predetermined distance from one another;

an upward flow splitting feature formed on the first lower surface of the first horizontal plate microbial support media by adjacent portions of two first protuberances, the first adjacent portions disposed above the second opening of a second protuberance of the second horizontal plate microbial support media, the upward flow splitting feature configured to split the flow of the liquid passing through the second opening; and an upward flow remixing feature formed in part by the second upper surface of the second horizontal plate microbial support media by adjacent portions of two second protuberances, the second adjacent portions disposed below the first opening of a first protuberance of the first horizontal plate microbial support media, the upward flow remixing feature configured to remix at least a portion of the flow of the liquid split by the upward flow splitting feature.

2. The microbial support media system of claim 1, wherein the upward flow splitting feature is configured to act as a first attachment site for a first biofilm.

3. The microbial support media system of claim 2, wherein the first biofilm is comprised mainly of methane producing microorganisms.

4. The microbial support media system of claim 2, wherein the upward flow splitting feature is configured to act as an impingement surface for the liquid flowing upward through the second opening such that the liquid contacts the first biofilm.

5. The microbial support media system of claim 4, wherein the liquid is as an upward flowing carrier liquid for suspended and colloidal solids.

6. The microbial support media system of claim 5, wherein the first biofilm captures suspended and colloidal solids from the liquid for digestions.

7. The microbial support media system of claim 6, wherein the first biofilm captures upward flowing carbon dioxide ($CO_2$) and hydrogen ($H_2$).

8. The microbial support media system of claim 7, wherein the carbon dioxide ($CO_2$) and hydrogen ($H_2$) are released in hydrolysis and acidogenesis reactions.

9. The microbial support media system of claim 2, wherein the upward flow remixing feature is configured to provide a second attachment site for a second biofilm.

10. The microbial support media system of claim 9, wherein the second biofilm is comprised mainly of hydrolysis bacteria and acidogenesis bacteria.

11. The microbial support media system of claim 1, wherein the first protuberances have a height selected from a range of one (1) inch to twelve (12) inches.

12. The microbial support media system of claim 1, wherein first side portions of the first protuberances that extend upward form an angle from the upper and lower surfaces of the first horizontal plate microbial support media, wherein the angle is selected from a first range of twenty (20) degrees to eighty (80) degrees.

13. The microbial support media system of claim 12, wherein the angle is selected from a second range of forty-five (45) degrees to sixty (60) degrees.

14. The microbial support media system of claim 1, wherein the first and second openings are an oval shape.

15. The microbial support media system of claim 4, further comprising biofilm attachment projections extending downward from the impingement surface of the upward flow splitting feature.

16. The microbial support media system of claim 5, wherein the biofilm attachment projections are configured to act as a third attachment site for the first biofilm.

17. A microbial support media system for an upward flow microbial digestion system, comprising:

a first horizontal plate microbial support media having a first upper surface and a first lower surface, the first horizontal plate microbial support media having a plurality of first protuberances, each of the first protuberances having a first base and a first upward end, each of the first protuberances extending upward from the first upper and lower surfaces at the first base to the first upward end in such a way that the first base of each of the first protuberances is wider than the first upward end, each first upward end having a first opening for allowing the upward flow of a liquid to pass through;

a second horizontal plate microbial support media having a second upper surface and a second lower surface, the second horizontal plate microbial support media having a plurality of second protuberances, each of the second protuberances having a second base and a second upward end, each of the second protuberances extending upward from the second upper and lower surfaces at the second base to the second upward end in such a way that the second base of each of the second protuberances is wider than the second upward end, each second upward end having a second opening for allowing the upward flow of the liquid to pass through, the first horizontal plate microbial support media disposed above the second horizontal plate microbial support media in such a way that the plurality of first protuberances and the plurality of second protuberances are offset a predetermined distance from one another;

an upward flow splitting feature formed on the first lower surface of the first horizontal plate microbial support media by first adjacent portions of two first protuberances, the first adjacent portions disposed above the second opening of a second protuberance of the second horizontal plate microbial support media, the upward flow splitting feature configured to split the flow of the liquid passing through the second opening, the upward flow splitting feature configured to act as an impingement surface for the liquid flowing upward through the second opening;

an upward flow remixing feature formed at least in part on the second upper surface of the second horizontal plate microbial support media by adjacent portions of two second protuberances, the adjacent portions disposed below the first opening of a first protuberance of the first horizontal plate microbial support media, the upward flow remixing feature configured to remix at least a portion of the flow of the liquid split by the upward flow splitting feature; and biofilm attachment projections extending downward from the impingement surface of the upward flow splitting feature, the biofilm attachment projections configured to act as a first attachment site for a first biofilm.

18. The microbial support media system of claim 17, wherein the upward flow remixing feature is configured to provide a second attachment site for a second biofilm.

19. The microbial support media system of claim 18, wherein the first biofilm is comprised mainly of methane producing microorganisms and the second biofilm is comprised mainly of hydrolysis bacteria and acidogenesis bacteria.

* * * * *